United States Patent [19]

Ruschke

[11] 4,190,426
[45] Feb. 26, 1980

[54] GAS SEPARATING AND VENTING FILTER

[75] Inventor: Ricky R. Ruschke, McHenry, Ill.

[73] Assignee: Baxter Travenol Laboratories, Inc., Deerfield, Ill.

[21] Appl. No.: 856,147

[22] Filed: Nov. 30, 1977

[51] Int. Cl.² ............................................. B01D 46/00
[52] U.S. Cl. ................................................ 55/185; 55/210;
55/310; 55/514; 55/528; 55/484; 128/214 R;
128/276; 137/854; 210/DIG. 23; 210/436
[58] Field of Search ............. 55/159, 185, 310, 385 R,
55/210, 385 C, 466, 486, 487, 482, 514, 527,
528, 484; 210/436, DIG. 23; 128/214 R, 214 C,
276; 137/854

[56] References Cited

U.S. PATENT DOCUMENTS

| 2,068,481 | 1/1937 | Brown | 137/854 |
|---|---|---|---|
| 3,149,758 | 9/1964 | Bush et al. | 210/DIG. 23 |
| 3,371,468 | 3/1968 | Shropshire | 55/16 |
| 3,506,130 | 4/1970 | Shaye | 210/DIG. 23 |
| 3,523,408 | 8/1970 | Rosenberg | 55/159 |
| 3,631,654 | 1/1972 | Riely et al. | 128/214 R |
| 3,650,093 | 3/1972 | Rosenberg | 55/159 |
| 3,696,932 | 10/1972 | Rosenberg | 210/437 |
| 3,701,433 | 10/1972 | Krakauer et al. | 210/436 |
| 3,778,971 | 12/1973 | Granger et al. | 55/159 |
| 3,803,810 | 4/1974 | Rosenberg | 128/214 R |
| 3,854,907 | 12/1974 | Rising | 210/DIG. 23 |
| 3,905,905 | 9/1975 | O'Leary et al. | 210/436 |
| 3,954,623 | 5/1976 | Hammer et al. | 210/DIG. 23 |
| 3,976,529 | 8/1976 | Weichselbaum | 128/214 R |
| 3,993,068 | 11/1976 | Forberg | 128/214 C |
| 3,998,255 | 12/1976 | Mather et al. | 55/310 |
| 4,004,587 | 1/1977 | Jess | 210/DIG. 23 |
| 4,009,714 | 3/1977 | Hammer | 128/214 C |
| 4,009,715 | 3/1977 | Forberg et al. | 128/214 R |
| 4,077,784 | 3/1978 | Vayrynen | 55/417 |

FOREIGN PATENT DOCUMENTS

| 2314753 | 6/1976 | France | 210/DIG. 23 |
|---|---|---|---|
| 1221625 | 2/1971 | United Kingdom | 210/DIG. 23 |

Primary Examiner—Bernard Nozick
Attorney, Agent, or Firm—Paul C. Flattery; John P. Kirby, Jr.; Gary W. McFarron

[57] ABSTRACT

A fluid filter is disclosed which separates gas from liquid and vents the separated gas from the filter. The filter includes a vented housing through which the fluid stream passes. Liquid-wetting filter means carried in the housing in the path of the fluid stream permits the passage of liquid only. Gas separated from the fluid is vented through vent opening means which is covered by a liquid-repellent filter to permit the passage of gas only. An automatic, pressure sensitive control means may be used to seal the vent opening means against the entry of ambient air but to automatically release separated gas from the filter. The liquid-repellent filter may be secured to the housing by a mechanical bond between the housing and a fibrous backing carried by the filter, or a continuous band of medical grade tape may be used to attach the filter to the housing.

11 Claims, 9 Drawing Figures

FIG. 1
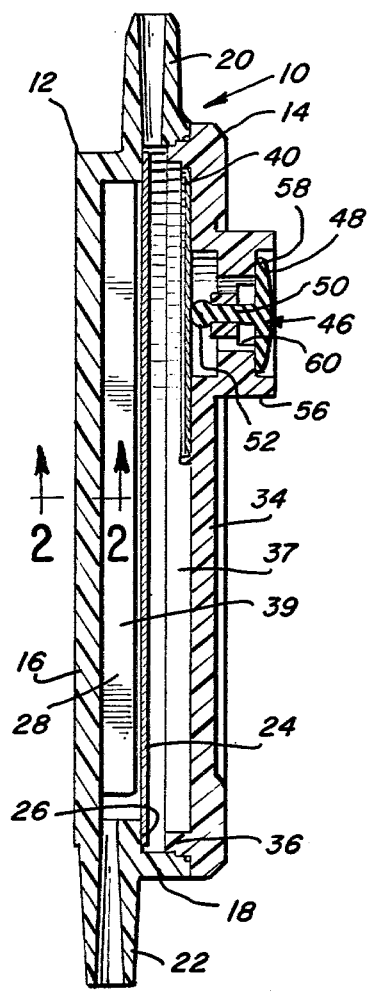
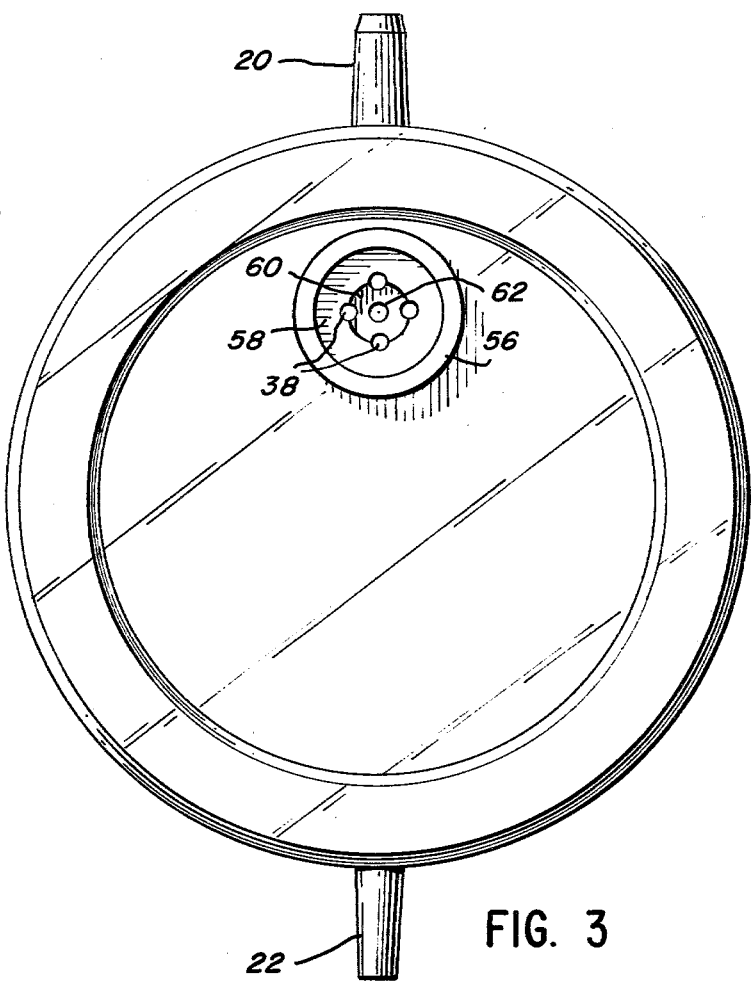
FIG. 3
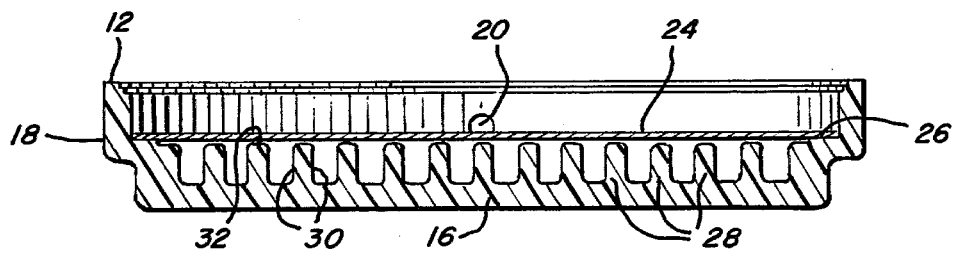
FIG. 2

GAS SEPARATING AND VENTING FILTER

The present invention relates generally to fluid filters which separate gas from liquid in a fluid stream and vent the gas. More particularly, the invention relates to such filters which are capable of separating gas from liquid in fluids which are administered to a living subject.

Fluid filters which utilize a porous membrane or other filter media which becomes resistant to the transmission of gas when wetted by liquid have been used in a wide variety of situations. One increasingly important use for such filters is in filtering blood, plasma, parenteral solution or other fluid, as the fluid is administered to a living subject, usually human. In the administration of such fluids, in addition to filtering out particulate matter and potentially harmful micro-organisms, it is preferred that any gas or air suspended or entrained in the fluid also be removed so as to eliminate any hazard of embolism from air or gas reaching the patient.

Present filters which have been used to remove gas from intravenous fluid have often included a liquid-wetting filter membrane which, when wetted, is resistant to the transmission of gas having a pressure below the so-called "bubble point", in combination with a liquid-repellent or non-wetting filter membrane through which the separated gas must pass before it is vented through openings in the filter housing. For filtering an aqueous solution, such filters are usually referred to respectively as hydrophilic (water-wetting) and a hydrophobic (water-repellent). A hydrophilic filter permits water to pass but is resistant to the passage of gas when wetted by water. A hydrophobic filter permits gas to pass but is resistant to the passage of water. The liquid-repellent filter membrane through which escaping gas must pass not only prevents leakage of liquid through the vent openings, but also, by its microporous construction, protects the filtering liquid against contamination from the ambient atmosphere. One example of a filter constructed with wetting and non-wetting filter membranes is shown in U.S. Pat. No. 3,523,408 to Rosenberg. There, the fluid is introduced between a pair of equally large, facing filter membranes, one of which is liquid-wetting and the other of which is liquid-repellent. Gas which is removed from the fluid by the liquid-wetting filter passes through the liquid-repellent filter and vents through open ports in the housing. Other filters of somewhat different construction but similar operation may be found in U.S. Pat. Nos. 3,854,907, 3,803,810, and 3,631,654.

Filters which have been made as described above, however, have several shortcomings. If the liquid-wetting filter is broken or otherwise fails so that it permits gas to pass with the liquid, ambient air can be aspirated directly through the vent openings and the liquid-repellent filter and into the liquid which is being administered, possibly resulting in embolism in the patient. This may occur, for example, when the filter is connected in such a manner that a column of liquid can develop below the filter and create a suction in the filter. Also, the use of equipment, such as pumps, in an administration therapy set may create a suction within the filter housing in certain situations.

Another hazard with the aforedescribed filters is that failure of the liquid-repellent filter would expose the solution or fluid to contamination from the ambient atmosphere.

Because of these hazards, some filters are constructed which intentionally permit passage of gas or air entrained in the solution, thereby avoiding the need for vent openings or a filter membrane exposed to the exterior. One such filter is described in U.S. Pat. No. 4,004,587. In those filters which have used a vent opening with a filter membrane in the path of venting gas, some have employed a seal over the vent opening to preclude the admission of outside air into the filter. However, the seals now in use must be manually removed or manipulated from time to time to permit separated gas to vent from the filter. Otherwise, separated gas will accumulate and may eventually block the flow of liquid through the filter. Manual venting is not preferred because it requires continual monitoring by an attendant or the patient, which is not always possible or practical. In addition, many of these seals are subject to being disabled or overridden by the attendant or patient so that the vent is always exposed to the exterior, with the potential hazards discussed above.

One filtration unit which uses a manual valve for priming or for releasing entrapped air is described in U.S. Pat. No. 3,954,623. There a push-button type resilient valve extends through a single vent opening in the housing and has an enlarged bulb inside the housing which seals against the edge of the vent opening. By pushing the valve, the bulb is forced away from the vent, permitting entrapped air to escape. The filter in U.S. Pat. No. 3,954,623 however, does not have a liquid-repellent filter to prevent liquid from escaping through the vent, rather it has a synthetic fiber batt between the valve and the filter housing. If wetted by escaping fluid during priming or routine venting, this batt may collapse and, no longer exerting force between the housing and the valve, permit leakage of fluid from the filter housing.

Present filters have also utilized relatively complex or inconvenient methods for mounting filter membranes in the filter housing. This is particularly true of the non-wetting filter membrane, which is often constructed of polytetrafluoroetheylene, perhaps better known under the trademark TEFLON. Because of its high melting point, polytetrafluoroetheylene is not compatible, e.g., for heat sealing, with filter housing materials of lower melting points. Thus, to adequately seal present filters, it has been necessary in many filters to use adhesive-type bonding which requires very careful assembly operations, or silicone ring seals tightly clamped around the periphery of the filter membrane. A filter with a silicone seal is illustrated in the U.S. Pat. No. 3,532,408 to Rosenberg. Such construction, of course, increases costs for materials as well as for labor in making the filter.

Accordingly it is a general object of the present invention to provide a gas separating and venting filter which does not suffer from the shortcomings described above. Another object is to provide a gas separating filter which permits separated gas to vent from the filter through a non-wetting membrane but does not permit ambient air to enter the filter and does not require continual monitoring. A further object of the invention is to provide more simple means for mounting non-wetting filters in the filter housing.

These and other objects are met by the present invention by providing a filter which employs a liquid-wetting filter to separate entrained gas from liquid and a liquid-repellent filter over vent openings to permit the separated gas to vent while preventing passage of liquid through the vent openings. Automatic vent control means, sensitive to the differential pressure between the trapped gas and atmospheric pressure, may be employed adjacent to the vent openings to automatically vent trapped gas from the filter and to seal the vent opening against the admission of outside air into the fluid stream at all other times.

For an automatic vent control means, this invention preferably employs a flexible, resilient umbrella valve with a canopy which overlies a plurality of vent openings. The flexibility of the canopy permits it to flex away from the vent openings upon application of pressure from the separated gas inside the filter housing which is greater than the ambient atmospheric pressure. After the gas is vented, the resilient canopy reseals the vent openings. When less than atmospheric pressure exists in the filter housing, that is, when there is a negative pressure differential, the canopy is drawn even tighter against the vent openings to even better seal them. Manual venting is also provided for by a recess adjacent to the vent openings and below the canopy. By depressing the canopy into the recess, the canopy portion over the vent openings is caused to invert or flare away from the vents, permitting the release of any separated gas which did not have sufficient pressure to automatically raise the umbrella canopy.

Also in accordance with the present invention, a relatively small liquid-repellent filter membrane of higher melting point than the filter housing is provided with a fibrous backing layer and is mounted against the inside of the housing, over the vent openings, by bonding the fibrous layer to the housing. The housing beneath the periphery of the liquid-repellent filter is heated until it melts sufficiently to fill interstices in the fibrous backing. After cooling, the plastic in the interstices hold the filter and fibrous backing securely to the housing. The liquid-repellent filter may also be simply attached to the housing by a continuous band of medical grade tape which overlaps the peripheral edge of the filter membrane and the adjoining portion of the housing. By heating the tape and applying pressure theragainst, the tape is caused to more securely adhere to the filter and housing and at the same time stresses in the tape are relieved.

The present invention is more specifically set forth in the following detailed description and the attached drawings, of which FIG. 1 is a vertical cross-sectional view of a filter embodying the present invention;

FIG. 2 is a sectional view taken along lines 2—2 of FIG. 1;

FIG. 3 is a top plan view of the filter of FIG. 1, but without the umbrella valve of FIG. 4;

Figure 4:
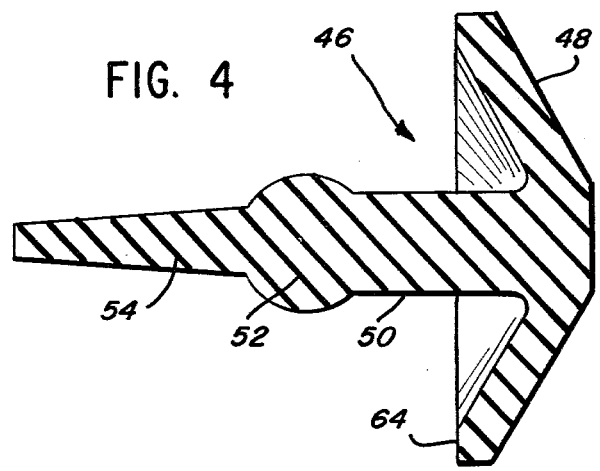
FIG. 4 is an enlarged cross-sectional view of the umbrella valve used in the filter of FIG. 1.

Turning now to a detailed description of the present invention, as shown in its preferred embodiment in the attached drawings, the present invention is embodied in a generally disc-shaped filter housing 10, which has a shallow base portion 12, and a cap 14 covering the base portion to form an internal chamber. The housing may be constructed from any material which is compatible with the fluid being filtered, but the material is preferably clear, so that the filtering action may be observed. For filtering parenteral solutions, the housing is preferably made of clear, rigid, methyl-acrylic type plastic, such as that available under the trademark PLEXIGLAS, Type DR, from the Rohm and Haas Co. of Philadelphia, Pa., U.S.A. This material is relatively inexpensive and easy to mold.

The shallow base portion 12 of the housing is of one-piece, integral, molded construction, with a flat, circular bottom wall 16 and a short side wall 18 extending perpendicularly from the periphery of the bottom wall.

For permitting flow into and from the housing, opening means in the form of inlet and outlet ports 20 and 22, respectively, are provided in the side wall 18 of the base portion 12. The ports are located 180° apart, on opposite sides of the base portion, so that the filter may be used in a vertical or hanging position, as would be found in a gravity-flow parenteral fluid administration set. Each port has a slightly tapered barrel, which extends outwardly from the side wall, and tapers toward the end for slidably receiving connector tubing or the like. A reversely tapered bore for fluid flow extends through the center of each barrel, and through the side wall.

For mounting a liquid-wetting filter membrane 24 in the base portion, a flat shoulder 26, generally parallel to the bottom wall 16, is provided continuously along the inside of side wall 18. The liquid-wetting membrane is flat, disc-shaped, and of the appropriate size so that the peripheral edge of the filter overlaps the shoulder. The edge of the membrane is then sealed to the shoulder by adhesive, heat-seal, high-frequency welding, or other available attachment means, such as using the edge of the cap 14 to clamp the filter in place.

In the preferred embodiment, for use in filtering aqueous parenteral solutions, the liquid-wetting filter membrane is hydrophilic and made of mixed esters of cellulose, which is compatible with the housing material and the aqueous parenteral solutions. The membrane has a mean average pore size ranging from about 0.1 to about 0.45 microns, and preferably about 0.22 microns to remove bacteria from the liquid being filtered. Such a filter material is wetted by water and resistant to the transmission of gas therethrough, so long as the gas pressure is below the bubble point of the material. The bubble point generally describes the differential pressure across the membrane at which gas will be forced through the wetted filter membrane, and, for the preferred material described above, is about 55-60 psid. This material is commercially available from the Millipore Corporation of Bedford, Mass., as Type GS Hydrophilic.

This preferred hydrophilic filter membrane 24 is attached to the base portion 12 by direct heat sealing before the cap 14 is attached. The flat, disc-shaped filter membrane is positioned in the base portion with the edges overlapping the shoulder 26. An annular heat-sealing surface or head, with a temperature substantially higher than the melting points of the filter membrane and the housing, is then pressed against the membrane along the shoulder until the membrane and shoulder have melted sufficiently to coalesce and form a uniform seal around the periphery of the filter membrane.

So that liquid flowing through the housing will pass through the liquid-wetting membrane 24, the inlet and outlet ports 20 and 22 are located on opposite sides of the shoulder 26, and, therefore, on opposite sides of the filter membrane 24. Specifically, the inlet port 20 is positioned in the portion of the side wall 18 above the shoulder, in other words, between the shoulder and the cap 14. The outlet port 22 is located in that portion of the side wall below the shoulder, between the shoulder and the bottom wall 16.

As best seen in FIG. 2, the base portion 12 of the housing 10 further includes a series of spaced, parallel ribs 28, which underlie and help support the relatively fragile liquid-wetting filter membrane 24. The ribs project perpendicularly from the bottom wall 16, and are of generally rectangular cross-section, each having a pair of parallel side surfaces 30 and a flat-top surface 32. The top surface is located just below the shoulder 26, so that it closely underlies the filter membrane and supports it against the upstream pressure of liquid being filtered. Otherwise, without support, the fragile filter membrane may over-flex and tear or burst from the pressure of the filtering liquid.

Figure 8:
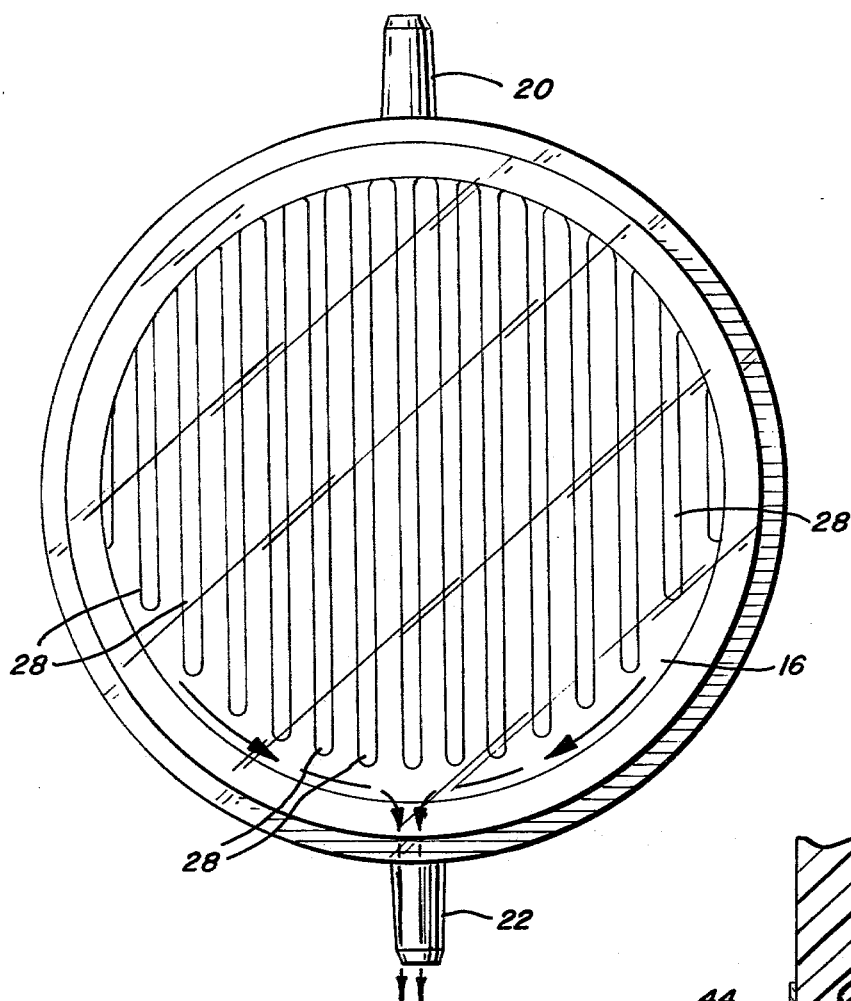
FIG. 8 is a bottom plan view of the filter of FIG. 1.

Channels formed between adjacent ribs 28 conduct filtered liquid to the outlet port 22. As noted earlier, the base portion is generally circular, and as best seen in FIG. 8, the ribs run parallel to an imaginary diametrical line between the inlet and outlet ports. The ribs do not extend completely across the base but terminate at locations spaced from the portion of the side wall on the outlet side of the housing. With this construction, liquid which filters through the membrane 24 is conducted to the outlet port via channels which are closed at the inlet side of the housing by the side wall 18, and open at the other end to a semicircular fluid passageway (indicated by arrows in FIG. 8) on the outlet side of the base portion which directs the liquid toward the outlet port.

The base portion 12 of the housing 10 is closed by the cap 14 which has a generally flat circular top wall 34 and a continuous peripheral flange 36 extending perpendicularly from the top wall for insertion into the base portion and of appropriate size to snugly engage the inside of the side wall 18. The cap is preferably sealed to the base portion by sonic welding, which is well known in the art, but other means may be used, such as adhesives or direct heat-sealing.

After the cap is attached, it can be seen that the housing is divided into two subchambers by the liquid-wetting filter membrane—a first subchamber 37 between the membrane 24 and the cap 14 and second subchamber 39 between the membrane 24 and the bottom wall 16 of the base portion 12. The inlet port 20 communicates with the first subchamber for directing fluid which may have both liquid and gas components thereinto. The liquid-wetting filter blocks the flow of gas, and thus only liquid is conducted into the second subchamber from which it exits through the outlet port 22.

For venting gas or air which is separated from fluid passing through the filter from the first subchamber, vent opening means in the form of four vent ports 38 are provided in the top wall of the cap, which is upstream of the liquid-wetting filter. The vent ports are located in a closely spaced relationship between the center of the cap and the inlet port 20, and preferably as close to the inlet port as possible, so that when the filter is used in a hanging position as shown in FIG. 1, separated gas or air which naturally rises from the liquid-wetting filter will be able to vent from the housing. This location of the vent ports makes the filter position sensitive in that the vents are preferably located higher than most of the housing.

To prevent liquid from escaping through the vent ports 38, liquid-repellent filter means such as a liquid-repellent filter membrane 40 is secured to the inside of the cap 14 over the vent ports. A variety of liquid-repellent filter membrane materials may be used, but for filtering aqueous parenteral solutions the membrane is hydrophobic and preferably made of polytetrafluoroethylene which is naturally water repellent. The pore size must be sufficiently small, about 8 microns or less, to adequately prevent the passage of liquid through the membrane. In addition, the pore size of this filter membrane should also be sufficiently small to filter out most bacteria, and a desirable mean average pore size range is from about 0.1 to about 3.0 microns, preferably about 0.22 microns.

Figure 5:
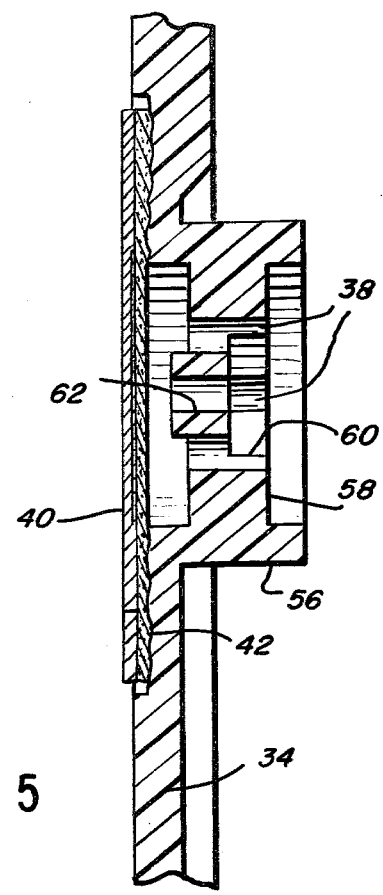
FIG. 5 is a partial sectional view of a filter embodying the present invention, showing the preferred method for attaching the liquid-repellent filter.

Because polytetrafluoroethylene melts at about 400° F., which is significantly higher than the approximate 350° F. at which the preferred housing material melts, which makes simple heat sealing difficult, the present invention includes two new and unique ways for attaching the filter membrane to the cap. The preferred method of attachment is best shown in FIG. 5. In this construction, the hydrophobic membrane is provided with a thin laminated layer of backing material 42 of fibrous construction. The membrane and backing layer must be sufficiently large to extend fully across the cover the vent ports 38 and overlap the area of the cap around the vent ports, but because of the position-sensitive location of the vent ports and the material used, the membrane 40 may be much smaller than the liquid-wetting membrane 24 which extends across the entire filter. In fact, the liquid-repellent membrane may be less than one-half of the area of the liquid-wetting membrane and satisfactory venting is obtained with a liquid-repellent membrane less than one-fifth the size of the liquid-wetting membrane.

The liquid-wetting membrane is positioned with the backing layer between the membrane and the cap. A heat sealing head, not shown, is then pressed against the membrane. The sealing head has a annular heated contact surface of appropriate size to engage at least a continuous portion of the peripheral membrane area overlapping the cap. The head is held in contact with the membrane until the portion of the cap therebeneath is heated enough to melt and become sufficiently liquid to flow or migrate into interstices between the fibers in the fibrous backing. The heat sealing head is then removed and the plastic cooled, the portions of plastic in the interstices in the fibrous backing forming a secure, watertight seal with the membrane and backing.

In the preferred embodiment, the backing material is made of non-woven polyester fiber, which is available already laminated to the polytetrafluoroethylene filter membrane, and is referred to as a Reemay backing, type LI0931, from the Gore-Tex Company of Elkton, Md., U.S.A. It has been found with these preferred materials that a satisfactory seal is created between the filter and a methyl acrylic cap when the heat sealing head is heated to about 350° F. and pressed against the filter membrane with a pressure of about 80 psi for approximately 3 seconds. Other combinations of temperatures, times, and pressures may also be used, but the example above is the preferred. Alternatively, ultrasonic welding techniques may be used to melt the plastic cap until plastic fills a continuous portion of the interstices in the fibrous backing.

Figure 9:
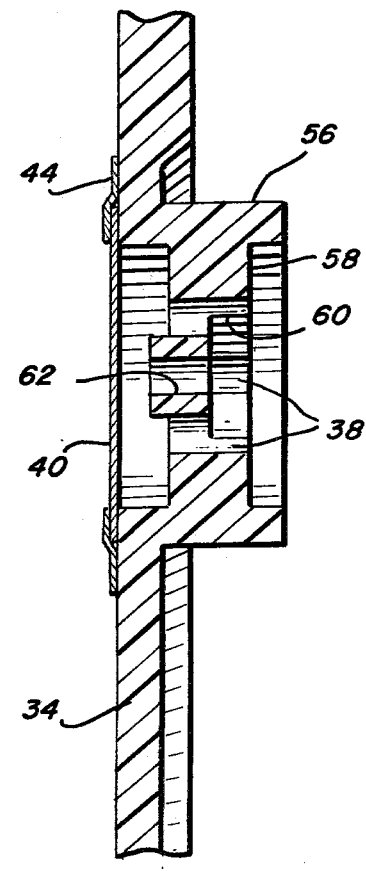
FIG. 9 is a partial sectional view showing an alternative method for attaching the liquid-repellent filter.

Another alternative means for attaching the liquid-repellent filter membrane 40 over the vent ports is shown in FIG. 9. In FIG. 9, as in FIG. 5, the filter membrane is of sufficient size to cover the vent ports 38. A continuous adhesive tape 44 overlaps the peripheral edge of the membrane and the inside surface of cap adjacent to the membrane. For use in intravenous solutions, the tape is preferably of medical grade, non-toxic and compatible with the fluid being filtered. One such tape would probably comprise an acrylic carrier with acrylic adhesive for compatibility with the solution being filtered. Medical tapes which have been considered for attaching the filter are available from 3M Company of St. Paul, Minnesota, U.S.A. under the trademarks BLENDREM and TRANSPORE.

In actual construction, the membrane 40 is disc-shaped and the tape has a ring or donut configuration. The membrane is first mounted against the adhesive side of the tape and then the tape and membrane are mounted against the inside surface of the cap, covering the vent ports. A heat sealing head like that described above, with an annular heating surface engageable against the tape, is then pressed against the tape and held in place with sufficient pressure and for sufficient time for the adhesive to become better activated and thereby provide better adhesion with the membrane and housing. It is also believed that heating relieves stresses in the acrylic tape which may occur during fabrication. It is presently understood that a better tape seal is obtained and stresses are relieved using a sealing head heated from about 150°-200° F. and pressing it against the tape at a pressure of about 50-70 psi for approximately 2-3 seconds. Whether the liquid-repellent membrane is attached to the cap by tape or mechanical bond, the cap and base portion are preferably sized so that the liquid-repellent and liquid-wetting membranes are at least five millimeters apart when the housing is assembled.

Although the liquid-repellent membrane 40 prevents liquid from escaping through the vent ports, if the filter is employed in a situation which permits less than atmospheric pressure to exist in the filter housing, i.e., a negative pressure differential, outside air will tend to enter through the liquid-repellent membrane and enter the solution being filtered. In such a situation, if the hydrophilic filter membrane 24 is not intact, for whatever reasons, outside air entering the solution would be conveyed directly into the patient, possibly resulting in embolism. To permit trapped gas to vent from the housing, and yet prevent outside air from entering during a less than atmospheric pressure situation in the housing, an automatic vent control means is provided which is sensitive to the differential pressure between the inside of the filter housing and the ambient atmosphere. In the illustrated embodiment of this invention, the automatic, pressure sensitive vent control means is provided in the form of an umbrella valve, generally at 46, which may be secured over the vent ports on the outside of cap 14. Referring to FIG. 4, the umbrella valve has a generally circular canopy or dome 48 which, in an unstressed position, extends at an acute angle to a centrally located stem 50. The stem has a middle bulbous portion 52 beyond which is a tapered shaft portion 54. The entire umbrella valve is one piece, integral construction and may be molded from rubber, preferably natural rubber, although any sufficiently flexible and resilient material that is compatible with the filter fluid may also be used.

The vent ports 38 are located in a raised cylindrical portion 56 of the cap 14. The cylindrical portion has a flat internal shoulder 58 surrounding the outer edge of a central cylindrical recess or depression defined by the wall surface 60. Referring briefly to FIG. 3 for clarity, the four vent ports are equally spaced, at 90° intervals around the peripheral wall 60 of the central recess.

The canopy 48 of the umbrella valve is of sufficient size that its periphery overlaps the inside shoulder 58, surrounding the vent ports 38 and completely covering them.

The umbrella valve 46 is mounted over the vent ports 28 by securing the stem to attachment means such as a central bore 62 in the bottom of the cylindrical recess. The bore is of substantially smaller diameter than the bulbous portion of the stem, which acts as an anchor to hold the umbrella valve in place. The tapered shaft portion 54 of the stem is inserted into the bore and pulled from the inside of the cap until the elastic bulbous portion passes through the bore and resumes its normal shape on the inside of the cap. The distance between the inside edge of the central bore 62 and the shoulder 58 is less than the length of stem between the canopy 48 and the bulbous portion 52. Thus, when the bulbous portion is drawn through the bore, the elastic stem is stretched, exerting an axial force on the canopy and drawing it into a normal tight, sealing contact against the shoulder. The tapered shaft portion is then snipped or cut from the bottom of the bulbous portion so as not to interfere with the liquid-repellent filter membrane 40. A flat contact surface 64 is provided along the underside of the peripheral portion of the canopy to aid in providing sealing contact with the shoulder.

Figure 6:
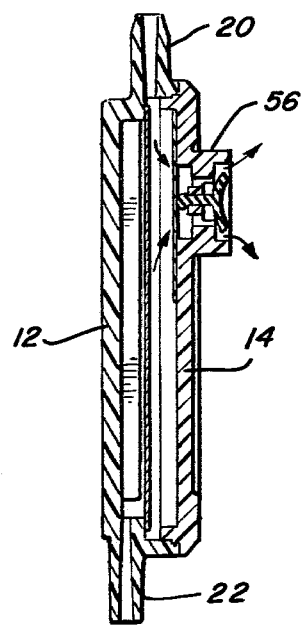
FIG. 6 is a sectional view of the filter of FIG. 1, illustrating automatic venting of gas from the filter.

With this construction, should the liquid-wetting filter fail, the elastic umbrella valve seals the vent ports 38 against the entry of outside air into the filter housing, and a vacuum inside the housing, or negative pressure differential between the housing and the ambient atmosphere only serves to draw the canopy into a tighter seal over the vent ports. While preventing outside air from entering, the flexible canopy nevertheless is sensitive to the pressure of gas accumulated inside the housing and permits such gas inside the housing to vent outwardly when its pressure is sufficiently greater than the atmospheric pressure i.e., a positive pressure differential. When entrained gas is separated from liquid by the liquid-wetting filter membrane, it rises toward the vent ports, which are located in the upper part of the housing. As particularly illustrated in FIG. 6, when the gas in the vent ports reaches sufficient pressure, it causes the flexible canopy to invert or flex upwardly, away from the shoulder 58 and vent ports, thereby permitting the separated gas to vent to the ambient atmosphere. After the gas has vented, the resilient canopy resumes its sealing position over the vent ports, preventing any outside air from entering the housing.

As noted earlier, one use for the filter is in hanging position in a parenteral solution administration set. The filter would be positioned below a parenteral solution container for example, about 15-18 inches below the container. With a 15-18 inch head of liquid, the pressure of entrained gas separated from the liquid will probably be somewhat more than $\frac{1}{2}$ psig, which is a positive differential pressure between the entrained gas and the ambient atmosphere. In such an application, the umbrella valve is preferably constructed to selectively release separated gas having a pressure of about ½ psig. The release pressure of the umbrella valve is a function of many variables, including the valve material, the thickness of the canopy, the tension in the stem and the degree of angle between the canopy and the stem, all of which may be readily determined by one skilled in the art after reading the description of this invention. However, as an example, one filter which released trapped gas at about ½ psig had the following features: in the cap, the distance between the inside edge of the bore 62 and the shoulder 58 was about 0.13 inches, the umbrella valve was made of natural rubber and had a canopy about 0.30 inches in diameter and about 0.03 inches thick, at an approximate acute angle of 61° with the stem; the distance between the top of the canopy and the center of the bulbous portion of the stem was about 0.192 inches; and the stem was uniformly 0.07 inches thick between the canopy and the bulbous portion.

On the other hand, the present filter is not limited to the particular application described above but may also be employed at a lower position in the administration set or in an "extension set" which is at about, or only slightly higher than, the level of venous entry. Under such conditions, a substantially greater head of liquid is created above the filter providing positive differential pressures of up to about 3 psig. So, depending on the particular application, the umbrella valve may be proportioned and assembled to vent at any selected pressure between about ½ and 3 psig. An umbrella valve with a higher release pressure usually also has a better sealing engagement between the umbrella canopy and the shoulder 58.

Figure 7:
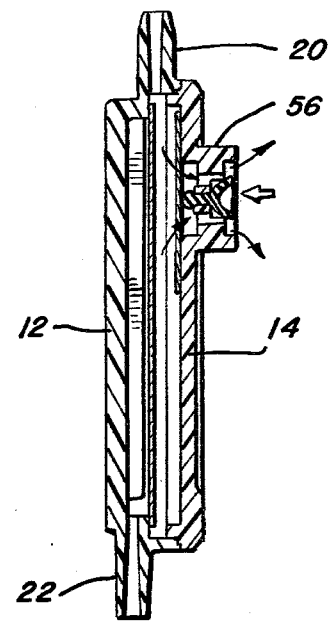
FIG. 7 is a sectional view of the filter of FIG. 1, illustrating manual venting of gas from the filter.

When the filter is used in systems which may not create sufficient gas pressure for automatic venting, the cylindrical recess defined by the wall surface 60 beneath the canopy provides a means for manually venting the filter housing. As described earlier, the vent ports are spaced around the recess. More particularly, and referring briefly to FIG. 3, the wall of the recess generally bisects each vent port. Now looking to FIG. 7, by manually depressing the center of the canopy 48 into the recess, a fulcrum-type engagement between the canopy and the edge of the recess causes the canopy to flex upwardly, thereby exposing at least a portion of the vent ports to the ambient atmosphere and permitting the separated gas to vent. Upon release of the umbrella it resumes the normal, sealing position. Because the umbrella valve is firmly anchored to the cap 14 by the bulbous portion and the canopy is surrounded by the walls of the raised portion of the cap, the umbrella valve is not easily removed or disabled so that the liquid-repellent filter would always be exposed to the ambient atmosphere.

This manual venting feature may be useful even in a filter in which it is desired, for whatever reason, that the umbrella valve not automatically vent. For example, an umbrella valve may be constructed of such proportions to provide an especially tight seal between the canopy and the shoulder. Such a valve may not automatically vent under the relatively low head pressures in an administration set. However, the present invention permits simple and effective manual venting of such a filter, for example, for priming the administration set.

It can therefore be seen from the description above that in accordance with the present invention a new and improved filter is provided for separating gas from liquid and venting the gas to the atmosphere. The filter is relatively simple and inexpensive to assemble. The liquid-repellent filter membrane with a fibrous backing for forming a mechanical bond with the plastic cap provides a much simpler and efficient method for attaching the filter, as does also the tape ring construction. A pressure sensitive vent control, such as the flexible umbrella valve, may also be employed to permit use of the filter in a variety of systems by providing an effective means for permitting gas to automatically vent while blocking the entry of outside air into the housing. And for gas of insufficient pressure to automatically vent through the umbrella type valve, the recess below the canopy permits manual flexing of the canopy to vent separated gas from the filter.

Although described for purposes of illustration in terms of the preferred embodiment, which is particularly useful for in-line filtration of parenteral solutions, the present invention is also intended to include such changes or modifications as come within the following claims, some of which changes or modifications may be immediately apparent and others of which may occur only after some study. For example, an umbrella valve configuration is not the only type vent control means which may be used, but other type systems, e.g., baffles or other types of controls which are sensitive to the differential pressure between the inside of the filter housing and the ambient atmosphere may also be used.

That which is claimed is:

1. A gas separating and venting filter comprising: a plastic heat-deformable plastic housing having walls defining an interior chamber, inlet opening means in said housing for conveying fluid into said chamber, one of said walls comprising liquid-wetting filter means for passing liquid only therethrough, outlet means downstream of said liquid-wetting filter means for conveying liquid therefrom, vent opening means in said housing communicating between the outside of said housing and said interior chamber to vent gas from said chamber, and planar liquid-repellent filter means covering said vent opening means and having a peripheral edge portion overlying said housing and sealed thereto to permit the passage of gas but to prevent liquid from escaping through said vent opening means, said liquid-repellent filter means comprising a plastic liquid-repellent filter membrane with a plastic fibrous backing disposed between said membrane and said housing, said filter means having a higher melt temperature than said housing, said seal between said filter means and said housing comprising a continuous mechanical bond formed between said fibrous backing and said housing in which portions of said housing fill the interstices in portions of said fibrous backing.

2. The filter of claim 1 in which said membrane is made of polytetrafluoroethylene and said housing is made of heat-deformable plastic of lower melting point than said membrane.

3. The filter of claim 2 in which said backing is polyester fiber and said housing is acrylic plastic.

4. In a gas separating and venting fluid filter comprising a housing including inlet opening means and outlet opening means, liquid-wetting filter means disposed in a flow path between said inlet and outlet opening to permit the passage of liquid only, vent opening means in said housing upstream of said liquid-wetting filter means to vent gas from the housing, the improvement comprising: vent control means associated with said vent opening means and being selectively operable to vent said gas automatically and manually, said vent control means comprising flexible resilient cover means carried exteriorly of said housing and including a portion normally overlying and sealing said vent opening means, said housing including at least one wall defining a recess on the exterior surface thereof adjacent said vent opening means and underlying said cover, whereby depression of said cover into said recess causes said cover to engage the edge of said wall and the portion of said cover overlying said vent opening means to flex away from said vent opening means, breaking the seal and permitting venting of gas from the filter, said resilient cover also being operable to flex away from said vent opening means and automatically vent gas when the gas pressure inside said housing is greater than atmospheric pressure.

5. The filter of claim 4 wherein said cover is operable to flex automatically to vent gas when the gas pressure inside said housing is between about one-half and three pounds per square inch greater than atmospheric pressure.

6. The filter of claim 4 in which said liquid-repellent filter is carried interiorly of said housing in the path of said venting gas to prevent liquid from escaping through said vent opening means.

7. The filter of claim 6 in which said liquid-repellent filter includes a liquid-repellent membrane overlying said opening means with a fibrous backing attached to said membrane and disposed between said membrane and said housing, said housing being of heat-deformable plastic, and a continuous mechanical bond being formed around said opening means between said backing and said housing with portions of said housing filling interstices in portions of said fibrous backing.

8. The filter of claim 4 in which said vent opening means comprises at least one port located along said wall.

9. The filter of claim 8 in which said recess is generally cylindrical and said resilient cover comprises an umbrella canopy carried over said recess and extending therebeyond to cover and seal said port.

10. The filter of claim 9 in which said vent opening means comprises a plurality of ports spaced along said wall.

11. The filter of claim 9 in which said umbrella includes a stem attachment extending through a center bore in said recess, said stem having a bulbous portion on the end thereof said bulbous portion being larger than said bore and disposed interiorly thereof.

* * * * *